United States Patent [19]

Howe

[11] 4,053,501

[45] Oct. 11, 1977

[54] ALKOXYCARBONYLBENZYLTRIALKYL-PHOSPHONIUM SALTS

[75] Inventor: Robert K. Howe, Bridgeton, Mo.

[73] Assignee: Monsanto Company, St. Louis, Mo.

[21] Appl. No.: 347,519

[22] Filed: Apr. 3, 1973

[51] Int. Cl.² .................... C07F 9/54; A01N 9/36
[52] U.S. Cl. ........................... 560/103; 71/76; 71/86; 71/87
[58] Field of Search ............. 260/476, 606.5 F, 476 R

[56] References Cited

U.S. PATENT DOCUMENTS 3,742,064  6/1973  Diamond et al. ............. 260/606.5 F Primary Examiner—James O. Thomas, Jr.
Assistant Examiner—Michael Shippen
Attorney, Agent, or Firm—Richard H. Shear; Donald W. Peterson

[57] ABSTRACT

A novel class of ortho or meta-alkoxycarbonylbenzyltrialkylphosphonium salts are prepared and demonstrate useful plant growth regulation when applied to desirable plants. Representative of this class of compounds is m-methoxycarbonylbenzyltributylphosphonium bromide.

1 Claim, No Drawings

ALKOXYCARBONYLBENZYLTRIALKYLPHOSPHONIUM SALTS

BACKGROUND OF THE INVENTION

This invention relates to a novel class of ortho or meta-alkoxycarbonylbenzyltrialkylphosphonium salts and to a method for regulating the natural growth or development of plants using said class of phosphonium compounds. The compounds of this invention are plant regulators which are defined by Congress in Public Law 92-516, the Federal Environmental Pesticide Control Act of 1972, section 2, subsection v, as any substance or mixture of substances intended through physiological action, for accelerating or retarding the rate of growth or rate of maturation, or for otherwise altering the behavior of plants or the produce thereof, but shall not include substances to the extent that they are intended as plant nutrients, trace elements, nutritional chemicals, plant inoculants, and soil amendments. In view of the ever increasing demand for plant products due to the rapid expansion of the world population, considerable research has been conducted to find chemical substances which can be beneficially utilized as plant regulators, such as, agents which retard vegetative growth or are useful for optimizing the yeilds of various crops.

Various phosphonium compounds are known. For example, U.S. Pat. No. 2,703,814 is directed to the preparation of phosphonium bromides and chlorides. U.S. Pat. No. 3,230,069 and U.S. Pat. No. 3,268323 are directed to classes of phosphonium compounds useful for the regulation of plant growth. Another class of phosphonium compounds is described in U.S. Pat. No. 3,281,365, useful in antiseptic detergent compositions. A further class of phosphonium compounds useful for controlling nematodes is shown in U.S. Pat. No. 3,642,989.

SUMMARY OF THE INVENTION

This invention is directed to novel class of substituted benzyltrialkylphosphonium salts characterized by having a alkoxycarbonyl substituent in the ortho or meta position of the benzyl ring. This novel class of chemical compounds is represented as follows:

Formula (1)

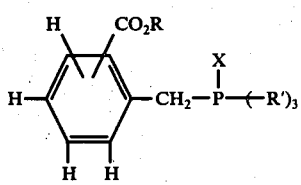

wherein R is alkyl of not more than four carbon atoms and is, for example, methyl, ethyl, propyl, isopropyl, butyl, sec-butyl or tert-butyl; wherein R' is alkyl of not more than four carbon atoms and is preferably propyl or butyl and most preferably butyl; and wherein X is Cl, Br, I, $SO_4$, $CO_3$, $NO_3$, or $PO_4$ and is preferably Br.

Another embodiment of this invention is the method of regulating the natural growth or development of plants which comprises applying to the plant an effective plant regulating amount of a compound of the formula

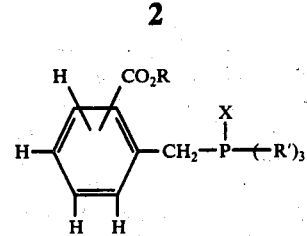

wherein R, R' and X are as defined above.

The alkoxycarbonyl substituent and its position on the benzyl ring is critical and provides a unique class of phosphonium compounds not previously described. The instant alkoxycarbonylbenzyl derivatives are effective for treating plants with a foliar application to regulate the plant's growth without substantial damage.

This invention is also directed to plant growth regulant compositions comprising an effective amount of the above-defined class of alkoxycarbonylbenzyltrialkylphosphonium salts and an adjuvant such as a surfactant.

DESCRIPTION OF THE INVENTION

In accordance with this invention a method is provided whereby viable plants are treated with a chemical substance which alters their natural growth or development to enhance the various agricultural or horticultural features of the plants. As employed herein, the term "natural growth or development" designates the normal life cycle of the plant in accordance with its genetics and its environment, in the absence of artificial, external influences.

The method of regulating plant growth provided by this invention is particularly useful for treating dicotyledonous plants to modify the vegetative growth, the flowering or fruit set or to optimize the yield. Representative crop plants which can be treated with the compounds of this invention are, for example, soybean (Glycine), cotton (Gossypium), beans (Phaseolus), coffee (coffea), tomato (Lycopersicon) and the like, which often do not obtain their yield capacity due to premature blossom drop or because of failure of the fruit to set.

For convenience, the term "active ingredient" will be used hereinafter to connote one or more of the ortho or meta-alkoxycarbonylbenzyltrialkylphosphonium salts as previously defined.

It is to be understood that the regulation of natural growth and development does not include killing or herbicidal action. Although phytotoxic or lethal amounts of the active ingredient might be employed to destroy certain plants, it is contemplated here to employ only such amounts of said active ingredient as will serve to regulate the natural growth and development of useful plants without substantial injury. As may be expected and as long understood by those skilled in the art, such effective plant regulating amounts will vary, not only with the particular active ingredient selected for treatment, but also with the regulatory effect to be achieved, the species of plant being treated and its stage of development, and whether a permanent or transient regulating effect is sought. Other factors which may bear upon the determination of an appropriate plant regulating amount include the plant growth medium, the manner in which the treatment is to be applied, weather conditions such as temperature or rainfall, and the like.

In accordance with the instant invention it has been found that desirable regulation of natural plant growth or development is achieved by application of the active ingredient to plants in various stages of development. Accordingly, in the practice of this invention the active ingredient can be applied to the plant in the seedling stage, flowering stage or fruiting stage and the like or can be applied sequentially to plants at more than one stage of development. Such application may be directly to one or more of the plant's parts, such as stems, leaves, flowers, fruit or the like. Generally, the application is made by spraying the plants using conventional techniques.

Regulation of the natural growth or development of plants by chemical treatment results from the effect of the chemical substance on the physiological processes of the plant and the effect of such substance may be manifested by the morphology of the plant. As should be readily apparent, said regulation may also result from a combined or sequential effect of the chemical manifesting a response in both physiology and morphology.

In general, regulation of the natural growth or development which leads to a morphological change in the plant is readily noticeable by visual observation. Such changes can be found in the size, shape, color or texture of the treated plant or any of its parts. Similarly, changes in the quantity of plant fruit or flowers can be simply noted.

On the other hand, regulation which leads to changes only in the physiological processes occur within the treated plant and are usually hidden from the eye of an observer. Changes of this type are most often in the production, location, storage or use of naturally occurring chemicals, including hormones, within the plant. Physiological changes in a plant often are recognized when followed by a subsequent change in morphology. Additionally, there are numerous analytical procedures known to those skilled in the art for determining the nature and magnitude of changes in the various physiological processes.

The individual compounds of the instant invention serve to regulate the natural growth or development of treated plants in a number of diverse ways, and it is to be understood that each compound may not produce identical regulatory effects on each plant species or at every rate of application. As stated above, responses will vary in accordance with the compound, the rate, the plant, etc.

A regulatory response demonstrated by the compounds useful in the practice of this invention can be generally termed retardation of vegetative growth and such a response has a wide variety of beneficial features. In certain plants this retardation of vegetative growth causes a diminution or elimination of apical dominance leading to a shorter main stem and increased lateral branching. This regulation of the natural growth or development of plants produces smaller, bushier plants which often demonstrate increased resistance to climatic extremes, pest infestations and the like. Thus, the method of this invention provides for plants that are in a good state of health and tends to produce more effective plants.

As illustrated in the treatments hereinafter presented, the individual compounds of this invention regulate the natural growth or development of treated dicotyledonous plants in numerous other and different respects. Included among these other regulatory effects are the inducing of axiallary bud development, the alteration of shape of canopy, the delay or acceleration of fruit or pod set, etc. Although regulatory effects such as those described above can be desirable, often it is the ultimate result of these effects upon the economic factor which is of primary significance in crop plants or upon the aesthetic factor in ornamental plants. Thus, it must be recognized that increases in yield of individual plants, increases in the yield per unit of cropping area, improvement in the quality of the plants' product, improvement in the plants virgor and reductions in the cost of harvesting and/or subsequent processing are all to be considered in any assessment of the consequence of an individual regulatory effect during the growth or development of a plant.

The practice of the method of this invention is particularly useful for improving the efficiency of dicotyledonous row crops such as soybean (Glycine). The application of the compounds of this invention to such growing crop plants often reduces the stature of the plants without the expected substantial reduction in seed yield. In this manner the plant's efficiency of production is improved and a means is provided for optimizing the crop by increasing the plant population per unit area and treating said crop with the active ingredient during its growth stage. Such reduction in plant stature also increases accessibility to the field for other treatments, cultivation and harvesting.

In selecting the appropriate nontoxic rate of application of the active ingredient, it will be recognized that precise dosages will be dependent upon the plant species being treated, the particular plant part or habitat to which application is made, the development stage of the plant, the particular chemical employed, the mode of application and various other factors known to those skilled in the art. In foliar treatment for the regulation of plant growth, the active ingredients are applied in amounts from about 0.05 to about 10 or more pounds per acre. Foliar applications of from 0.1 to 2 pounds of the active ingredient per acre are preferred. In applications to the soil habitat of the plants the active ingredients are applied in amounts of from about 0.1 to about 20 pounds per acre or more. Preferably, the active ingredients are applied to the soil at a rate of from 1 to 10 pounds per acre. Foliar application to plants at the blooming stage, e.g., 10% blossoms, are particularly advantageous and are preferred.

PREPARATION OF THE COMPOUNDS

The compounds of the invention can be prepared by the reaction of a suitable α-halo-o or m toluoyl ester and trialkylphosphine using known methods such as disclosed in U.S. Pat. No. 2,703,814. Where the desired phosphonium salt is a halide, such as, Cl, Br or I, it can be prepared directly from the appropriate α-halo-toluoyl ester and trialkylphosphine. Where the desired phosphonium salt is the carbonate, nitrate sulfate or phosphate, it is readily prepared by an appropriate ion exchange with the phosphonium halides using known procedures such as disclosed in U.S. Pat. No. 3,268,323.

The α-halo-toluoyl esters can be prepared by the reaction of αhalo-toluoylchloride and an alcohol shown schematically as:

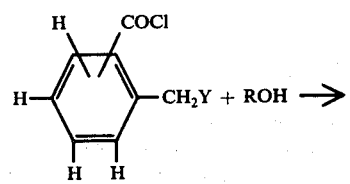

-continued

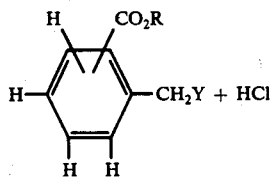

where R is as previously defined and Y is Cl, Br or I.

The above α-halo-toluoylchloride can be prepared in a known manner. For example, treatment of m-toluoyl chloride in benzene with an equal mol amount of N-bromosuccinimide at reflux gives a mixture of toluoylchlorides consisting of approximately 65% α-bromo-m-toluoylchloride. Where α-halo o toluoylchloride is desired, it can be readily prepared by the reaction of thionyl chloride and α-bromo-o-toluic acid prepared in a known manner from phthalide and hydrogen bromide in acetic acid.

An alternate method of preparing the compounds of this invention is the preparation of ortho-or meta carboxybenzyltrialkylphosphonium halide and reacting the compound with thionyl chloride to form the carbonylchloride derivative which is reacted with a suitable alcohol to form the desired alkoxycarbonyltrialkylphosphonium halide. This alternative method is preferred in that it provides the desired product which is readily crystallized and purified. The α-halotoluic acid and the carboxylbenzyltrialkylphosphonium halide are readily obtained in substantially pure form and subsequent reactions are relatively clean, producing products in high purity.

Further details of the compounds of this invention and their preparation are found in the following nonlimiting examples. All parts and percentages are by weight and degrees are in centigrade unless otherwise specified.

EXAMPLE I

A solution of 22.9 g (0.10 mol) of methyl m-(bromomethyl) benzoate and about 20.2 g (0.10 mol) of tri-n-butylphosphine in 150 ml of benzene in a suitable vessel is stirred at reflux for about 17 hours. The solution is cooled and 250 ml of ether is slowly added along with seed crystals. The resultant solid is collected and washed with ether to yield about 37.9 g (88%) of m-methoxycarbonylbenzyltributylphosphonium bromide, a white solid having a melting point of 144°–146°, and having a structure in accordance with formula (1) which is confirmed by nuclear magnetic resonance (nmr).

Anal. Calcd. for $C_{21}H_{36}BrO_2P$: C, 58.47; H, 8.41; Found: C, 58.22; H, 8.38.

EXAMPLE II

A mixture of 1 g of benzoyl peroxide, 178 g (1.0 mol) of N-bromosuccinimide, and 153 g (0.99 mol) of m-toluoyl chloride in 1400 ml of benzene in a suitable vessel is stirred at reflux using an infrared heat lamp for 2.3 hours. An nmr spectrum shows the reaction mixture to consist of 23% m-toluoyl chloride, 65% α-bromo-m-toluoyl chloride and 12% α, α-dibromo-m-toluoyl chloride. The mixture is concentrated under vacuum to about 300 ml, is filtered to remove succinimide, and is further concentrated at 90° (0.6 mm) for several minutes to give 214.8 g of a magenta liquid that contains about 16.5% m-toluoyl chloride, 69% α-bromo-m-toluoyl chloride, and 14.5% α, α-dibromo-m-toluoyl chloride.

A mixture of 43 g (about 0.20 mol) of the above mixture and about 12.62 (0.21 mol) of propyl alcohol is heated in a suitable vessel equipped with a reflux condenser, in an oil bath at 105° for 20 minutes, then is held under aspirator vacuum for 20 minutes at 80° to remove HCl fumes, and then is distilled. The cut with bp 105–115° (0.2 mm), 27.8 g, consists of 86% propyl α-bromo-m-toluate and 14% propyl, α, α-dibromo-m-toluate. A 14 g (0.045 mol of propyl-α-bromo-m-toluate) sample of the mixture is placed in a vessel and stirred with 8.48 g (0.042 mol) of tributylphosphine in 200 ml of ether under $N_2$ for 24 hours. The resultant white solid, 18.8 g, mp 112°–117°, is crystallized once from ethyl acetate-either to give 9.5 g of solid, mp 124°–125°. Recrystallization of this solid from ethyl acetate yields 6.5 g of m-propoxycarbonylbenzyltributylphosphonium bromide having a mp 126°–127° and a nmr spectrum consistent with the structure of formula (1).

Anal. Calcd. for $C_{23}H_{40}BrO_2P$: C, 60.13; H, 8.78; Found: C, 59.85; H, 8.77.

EXAMPLE III

To a vessel containing 20 g (about 0.093 mol) of crude α-bromo-m-toluoyl chloride and 6 g (0.10 mol) of isopropyl alcohol in 50 ml of ether is added, with cooling, about 10 g (0.093 mol) of 2,6-lutidine. After about 3 hours, 4.3 g of solid 2,6-lutidine hydrochloride is filtered off. After an additional 21 hours, 100 ml of ether is added and the mixture is filtered to give an additional 5.4 g of 2,6-lutidine hydrochloride. The filtrate is washed with 2 × 100 ml of ice water, two 100 ml portions of cold dilute hydrogen bromide, 100 ml of ice water and two 100 ml portions of ice cold sodium bicarbonate solution and the ether layer is dried over calcium sulfate and concentrated under vacuum to yield 17.6 g oil. To this oil is added 16.0 g (0.079 mol) of tributylphosphine in 100 ml of acetonitrile and is heated at reflux under $N_2$ for about 70 minutes then concentrated under vacuum to a black oil. The oil is triturated twice with 200 ml of ether and chromatographed on 150 g acid Woelm Act. I alumina with benzene. The first liter of eluate provides 15.3 g of solid which is crystallized twice from ethylacetate containing a small portion of acetonitrile to yield 6.4 g of m-isopropoxycarbonylbenzyltributylphosphonium bromide, a white solid having a melting point of 151°–153°.

Anal. Calcd. for $C_{23}H_{40}BrO_2P$: C, 60.13; H, 8.78; Found: C, 60.36; H, 8.81.

EXAMPLE IV

To a suitable vessel containing 14.3 g (0.0625 mol) of methyl α-bromo-m-toluate in 75 ml of acetonitrile is added 10.0 g (0.0625 mol) of tripropylphosphine under nitrogen. The solution is held at reflux under nitrogen for 45 minutes and is concentrated under vacuum to yield 24 g of a white solid. The solid is crystallized twice from acetonitrile-ethyl acetate to yield 14.3 g of m-methoxycarbonylbenzyltripropylphosphonium bromide having a melting point of 173°–175°.

Anal. calcd. for $C_{18}H_{30}BrO_2P$: C, 55.53; H, 7.77; Found: C, 55.45; H, 7.54.

EXAMPLE V

To a suitable vessel containing about 16.2 g of an approximate 50:50 mixture of methyl α-chloro-o-toluate and methyl α-bromo-o-toluate is added 100 ml of acetonitrile and 17.2 g (0.085 mol) of tributylphosphine and held at reflux under nitrogen for about 45 minutes. The solvent is removed under vacuum and the residue is dissolved in 370 ml of water. The aqueous solution is extracted twice with ether and added to a solution of 102 g (1.0 mol) of sodium bromide in 150 ml of water. This mixture is extracted with three 150 ml portions of chloroform. The chloroform extracts are combined, dried over calcium sulfate and concentrated under vacuum to 36.3 g of colorless oil. Two triturations of this oil with ether provides a white solid which upon recrystallization from ethyl acetate-ether yields approximately 24.6 g of o-methoxycarbonylbenzyltributylphosphonium bromide having a melting point of 65°–66°.

Anal. Calcd. for $C_{21}H_{36}BrO_2P$: C, 58.47; H, 8.41; Br, 18.52; Found: C, 58.26; H, 8.51; Br, 18.32.

EXAMPLE VI

Using the procedure of Example V, but sbustituting a mixture of propyl α-chloro-o-toluate and propyl α-bromo-o-toluate, prepared from propyl alcohol and α-bromo-o-toluoyl chloride, for the toluate mixture of Example V provides an oil which upon triturating several times with ether and precipitating as an oil from ethyl acetate with ether and drying yields 18.7 g of o-propoxycarbonylbenzyltributylphosphonium bromide, an oil having a structure in accordance with formula (1) which is confirmed by nmr spectral analysis.

Anal. Calcd. for $C_{23}H_{40}BrO_2P$: C, 60.13; H, 8.78; Found: C, 60.25; H, 8.92.

EXAMPLE VII

A solution of 10.0 g (0.024 mol) of m-carboxybenzyltributylphosphonium bromide and 10 ml (16.5 g, 0.139 mol) of thionyl chloride in a suitable vessel is heated on a steam bath for about 30 minutes and then poured into 50 ml of ethanol with stirring (exothermic). The solution is heated on a steam bath for about 10 minutes and then concentrated under vacuum. The residue is triturated with 150 ml of water and the solution is extracted twice with ether. The aqueous layer is separated and added to a saturated solution of 40 g sodium bromide in water. The resultant mixture is extracted with three 60 ml portions of chloroform. The extracts are combined, dried over calcium sulfate and concentrated under vacuum to give 13.9 g of oil. Dissolution of the oil in 50 ml of ethyl acetate and scratching yields 7.1 g of m-ethyoxycarbonylbenzyltributylphosphonium bromide, a white solid having a mp 142°–144° and a structure in accordance with formula (1 ) confirmed by nmr spectral analysis.

Anal. Calcd. for $C_{22}H_{38}BrO_2P$: C, 59.32; H, 8.60; Found: C, 59.22; H, 8.56.

EXAMPLE VIII

Using the procedure of Example VII but replacing the ethanol with n-butanol yields m-butoxycarbonyltributylphosphonium bromide, a white solid having a mp of 110°–112°.

Anal. Calcd. for $C_{24}H_{42}BrO_2P$: C, 60.88; H, 8.94; Found: C, 61.06; H, 8.94.

EXAMPLE IX

A solution of 7.0 g of m-methoxycarbonylbenzyltributylphosphonium bromide (Example I) in 90 ml of water is added to 30 g of sodium iodide in 40 ml of water with stirring. The resultant solid is crystallized twice from ethyl acetate to yield 4.2 g of m-methoxycarbonyltributylphosphonium iodide having a mp 143°–144°.

Anal. Calcd. for $C_{21}H_{36}IO_2P$: C, 52.72; H, 7.59; Found C, 52.93; H, 7.81.

Other compounds of this invention which can be prepared in accordance with the above examples include for example:
X - o-methoxycarbonylbenzyltriethylphosphonium chloride
XI - o-butoxycarbonylbenzyltripropylphosphonium bromide XII - m-propoxycarbonylbenzyltrimethylphosphonium bromide XIII - m-ethoxycarbonylbenzyltributylphosphonium iodide XIV - o-methoxycarbonylbenzyltributylphosphonium chloride XV - m-propoxycarbonylbenzyltriethylphosphonium bromide XVI - m-ethoxycarbonylbenzyltributylphosphonium bromide XVII - o-propoxycarbonylbenzyltripropylphosphonium bromide XIX - o-methoxycarbonyltributylphosphonium iodide Generally, the compounds are soluble in water and organic solvents such as acetone, ethanol, dimethylformamide, benzene, chloroform and the like.

The acute oral toxicity of a representative compound of this invention is considerably less than that reported for the previously known compound. For example, m-methoxycarbonylbenzyltributylphosphonium bromide has an acute oral $LD_{50}$ to rats of approximately 1580 mg/kg and is considered slightly toxic while 2,4-dichlorobenzyltributylphosphonium chloride (PHOSFON) has a reported $LD_{50}$ to rats of about 178 mg/kg and is considered moderately toxic.

PLANT GROWTH REGULATING COMPOSITIONS

Another embodiment of this invention is a plant growth regulating composition comprising an adjuvant and an effective plant growth regulating amount of a compound of formula (1).

The plant growth regulating compositions are particularly effective for practicing the method of regulating the natural growth or development of plants provided by this invention. In view of the activity of the active ingredients at low rates of application, it is desirable to use compositions comprising an effective amount of the active ingredient and an adjuvant to facilitate a uniform distribution of the compound on the plants. Adjuvant, as used herein, includes one or more materials in liquid or solid form. Thus, suitable adjuvants are diluents, extenders, carriers, surfactants, foaming agents, conditioning agents, solvents and, usually, combinations thereof. The compositions can be in numerous forms, such as, dusts, powders, water soluble powders, wettable powders, solutions, foams, dispersions or emulsions. Generally, it is preferred to use one or more surfactants in the plant growth-regulating compositions which aid in wetting the treated plant surface and for providing stable dispersions of the active ingredient in various inert carriers or diluents in the composition or added to the composition prior to application to the plants. Suitable surfactants which can be employed in the compositions of this invention are well known surface active agents, such as, wetting agents, emulsifiers, dispersing agents and can be nonionic, anionic or cationic. Preferred surfactants are the nonionic or the anionic type which are widely used in compositions employed in agronomic treatments. Representative nonionic surfactants are polyoxyethylene esters of fatty acids, octylphenyl polyethylene glycol ethers, polyoxyethylene derivatives of long-chain alcohols and the like. Representative anionic surfactants are alkali and alkaline earth salts of alkylarylsulfonic acids such as sodium lauryl sulfonate, dialkyl sodium sulfosuccinate esters and the like. Such surfactants are well known and reference is made to U.S. Pat. No. 2,547,724 for detailed examples of same.

Usually the plant growth-regulating compositions of this invention take the form of a concentrate which can be readily extended with an inert carrier prior to application to the plants. Said concentrates in liquid form consist of a solvent, surfactant and about 25 to 75% by weight of the active ingredient. These liquid concentrates can be diluted with water to provide a composition, suitable for application to plants, which contains from about 0.1 to about 15% by weight of the active ingredient. Concentrates in solid form are, for example, water soluble powders consisting of finely divided solids such as calcium silicate, surfactant and from about 5 to 80% or more by weight of the active ingredient which are diluted with water prior to applying to the plants.

A representative plant growth regulating composition in the form of a concentrate in solid form is set forth below.

EXAMPLE XX

Approximately 8 parts of nonylphenol-ethylene oxide condensate (STEROX NJ, surfactant) is added to 4 parts of calcium silicate (Microcel E, absorbent) and blended sufficiently to absorb the liquid surfactant. About 8 parts of monoammonium phosphate is added to the blend which is then added to 80 parts of m-methoxycarbonylbenzyltributylphosphonium bromide in a suitable powder blender to form a uniform mixture of the active ingredient in the form of a free flowing powder which is substantially soluble in water.

PLANT GROWTH REGULATING EVALUATIONS

The useful and unexpected plant growth regulating properties of the compounds of the foregoing formula (1) are demonstrated by exemplary tests set forth below as Test A. In the following Tests A and B the chemical was applied as an aqueous composition at the equivalent rate of active ingredient indicated. The aqueous compositions were prepared by solubilizing the required amount of the chemical in a volume of acetone which is further admixed with a like volume of 0.5% by weight aqueous solution of polysorbitan monolaurate (Tween Twenty surfactant), to provide sufficient composition which is applied at the rate equivalent to 200 gallons per acre to apply the chemical at the equivalent rate indicated.

Test A

A number of soybean plants, representative of dicotyledonous plants, are grown from seed in aluminum pans in a greenhouse for a period of approximately one week to the primary leaf stage. The plants are thinned to three uniform plants in each pan and the height of each plant is measured to the terminal bud and the average height is noted. One pan containing three soybean plants is used for each chemical treatment and four pans are not treated and used as a control. The aqueous composition of the chemical is then applied to the pan of growing plants by overhead spray at an established rate expressed as pounds per acre. The treated pans along with the control pans are watered from below, fertilized and otherwise maintained in a greenhouse under uniform growth conditions. Two weeks after application of the chemical the average height of the plants in the treated pan is determined as above and the difference in the average height before and two weeks after application represents the development of the treated plants. This development in growth of the treated plants is compared to the average development in growth of the plants in the control pans during the same period of time. A variation of 25% or more in the development of at least two-thirds of the treated plants when compared to the development of the control plants demonstrates that the chemical is effective for regulating the natural growth or development of the plants. Accordingly, a chemical is considered effective when the treated plants manifest at least 25% decrease in height development when compared to the untreated control plants, i.e. retardation of vegetative growth.

Using the procedure of Test A, retardation of vegetative growth in excess of 25% was obtained with representative compounds of this invention at the equivalent rate of application indicated below.

| Compound of Example | lbs/Acre | Other Observed Modifications |
| --- | --- | --- |
| I | 1.2 | dark foliar color |
|  | 0.6 | dark foliar color |
| II | 1.2 |  |
|  | 0.6 | dark foliar color |
| III | 1.2 |  |
|  | 0.6 |  |
| IV | 1.2 |  |
|  | 0.6 |  |
| V | 1.2 | dark foliar color, sl. leaf burn |
|  | 0.6 | dark foliar color, sl. leaf burn |
| VI | 1.2 | dark foliar color, sl. leaf burn |
|  | 0.6 | dark foliar color, sl. leaf burn |
| VII | 1.2 | dark foliar color |
|  | 0.6 | dark foliar color |
| VIII | 1.2 | dark foliar color |
| IX | 1.2 | sl. leaf burn |
|  | 0.6 |  |
| XIV | 1.2 | sl. leaf burn |
|  | 0.6 | sl. leaf burn |
| XIX | 1.2 | dark foliar color |
|  | 0.6 | dark foliar color |

The dark foliar color observed in the foregoing tests results in a darker green plant and demonstrates higher chlorophyll activity indicative of improved rates of photosynthesis. The slight leaf burn observed in some of the tests is limited to the voliage actually treated and is not observed in the new growth nor does it appear to be detrimental to the plants' development. Although additional tests were run at higher and lower rates of application, the rates recited above are indicative of the type of plant growth regulation obtained with the active ingredients of this invention when applied to plants at an early stage of growth.

The desirable plant growth regulating properties of the compounds of this invention are particularly unexpected since closely related compounds do not perform in the same manner. In tests conducted in accordance with Test A, m-carboxybenzyltributylphosphonium bromide and p-methoxycarbonyltributylphosphonium bromide did not demonstrate any significant plant growth regulation and were categorized as inactive, thus demonstrating the criticality of the alkoxycarbonyl group and its position on the benzyl ring.

Test B

In this evaluation soybean plants growing in individual pots which were 4 weeks old (3–4 trifoliate stage) and 6 weeks old (5–6 trifoliate stage) were used for each application of chemical. An overhead spray of the aqueous composition of the chemical is applied to 2 pots at each growth stage at an equivalent rate as indicated below. Two to four sets of plants which receive no chemical application are included and serve as controls. All of the pots are maintained under good growing conditions and are watered and are uniformly fertilized under uniform conditions. Two weeks after the application of the chemical the growth responses of the treated plants are compared with that of the control plants. The total height of the plant is measured to the tip of the terminal bud. A decrease of 15% or more in the average total height of the treated plants, when compared to that of the control plants, demonstrates that the chemical is effective for regulating the natural growth or development of the plants. In addition to this retardation of vegetative growth, other observations indicating a response in the plants treated with chemicals of this invention were noted.

Employing the procedure of Test B representative compounds of this invention were effective in reducing the total height of the plant in excess of 15% at the equivalent rate of application indicated below to the 4 and 6 week old plants.

| Compound of Example | lbs/acre | Other Observed Modifications |
|---|---|---|
| II | 2.5 | dark foliar color, axillary bud development |
| III | 0.25 | dark foliar color, axillary bud development, leaf alteration |
| VII | 0.5 | dark foliar color |
| VIII | 0.5 | dark foliar color |
| IX | 0.5 | dark foliar color |

The compound of Example I was used as the active ingredient in tests on various crops conducted in field plots.

Field plots of tomato plants, variety C-28, determinate processing type, were treated when the second flower cluster was formed but not open with a water solution of the composition of Example XX at rates equivalent to 0.5 and 2.0 pounds per acre of active ingredient. Each treatment was replicated four times as well as untreated plots of plants which served as control for comparison purposes. Approximately 8 weeks after treatment the plots were harvested and the treated plants were compared to the control plants. Neither treatment resulted in any appreciable morphological change in the plants which were of substantially equal in height as the untreated control plants. The tomato yield from each treatment was analyzed by weight and number and compared to the control for number of fruit per plant, weight per fruit and weight yield per plant using random selected plants and for weight yield per plot using the total yield of the plot. The 2 pounds per acre treatment demonstrated a 3% improvement in number per plant, about 9% improvement in fruit size, 12 % improvement in yield per plant and 14% improvement in yield per plot. The 0.5 pound per acre treatment provided a 16% increase in number per plant, 11% increase in fruit size, 28% increase in yield per plant and 16% increase in total yield per plot. Thus, the 0.5 pound per acre rate of application of the compound of Example I to tomato plants was the most effective in improving the yield of the plants.

A water solution of the composition of Example XX was applied to cotton growing in field plots at the onset of flowering. The application rate used was about 0.5 pound per acre of active ingredient using about 18 per acre of solution which provided adequate wetting of the foliage without runoff. At maturity the treated plants were compared to untreated control plants. No effect on the plant height of the treated plants was observed. The treated plants demonstrated improvement in the number of flowers and bolls and increased weight of see yield per plant.

Numerous field plots of soybean plants growing in various row spacings, for example, 10, 20 and 30 inch rows and various population densities were treated with a water solution of the composition of Example XX at rates equivalent to 1.0, 0.5 and 0.25 pounds per acre of active ingredient. The applications were made to the plants when the plants were beginning to blossom, approximately 10% blooms. At harvest the treated plants were compared to untreated control plants growing under the same conditions of row spacing and population density. These treatments provided a means of reducing the height of the plants generally in excess of 15 % without damage to the plant or alteration in the overall seed yield of the plants. Usually the 0.05 pound per acre treatment was the most effective.

In utilizing the methods and compositions of this invention, it is often advantageous to treat dicotyledonous crops which are beginning to blossom in order to elicit a growth response to optimize the plants' efficiency in producing fruit.

The methods of this invention can be conveniently carried out in conjunction with agronomic practices such as treating the plants with insecticides, fungicides, nematocides, fertilizer and the like. The application of compositions containing an active ingredient as herein defined and other agricultural chemicals such as selective herbicides, insecticides, fungicides, fertilizers, nematocides and the like are particularly advantageous for obtaining the desired results with minimum treatment costs.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

The embodiments of the invention in which an exclusive property or privilege is claimed are defined as follows:

1. The compound m-methoxycarbonylbenzyltributylphosphonium bromide.

* * * * *